US008666782B2

(12) United States Patent
Thierman (10) Patent No.: US 8,666,782 B2
(45) Date of Patent: Mar. 4, 2014

(54) SYSTEM AND METHOD FOR FORM RECORD PROCESSING

(75) Inventor: Jonathan S. Thierman, Baltimore, MD (US)

(73) Assignee: Sure-Shot Medical Device, Inc., Baltimore, MD (US)

( * ) Notice: Subject to any disclaimer, the term of this patent is extended or adjusted under 35 U.S.C. 154(b) by 318 days.

(21) Appl. No.: 12/829,751

(22) Filed: Jul. 2, 2010

(65) Prior Publication Data

US 2012/0004931 A1    Jan. 5, 2012

(51) Int. Cl.
  *G06Q 50/00*    (2012.01)
  *G06Q 10/00*    (2012.01)
(52) U.S. Cl.
  USPC ............................................................ 705/3
(58) Field of Classification Search
  USPC ........................................................ 705/2–3
  See application file for complete search history.

(56) References Cited

U.S. PATENT DOCUMENTS

| 5,317,733 | A  | * | 5/1994  | Murdock ................................ 1/1 |
| 5,664,109 | A  | * | 9/1997  | Johnson et al. .................... 705/2 |
| 6,047,259 | A  | * | 4/2000  | Campbell et al. ................. 705/3 |
| 2004/0078219 | A1 | * | 4/2004  | Kaylor et al. ...................... 705/2 |
| 2006/0074719 | A1 | * | 4/2006  | Horner ............................... 705/3 |
| 2007/0279187 | A1 | * | 12/2007 | Hekmatpour et al. ........ 340/5.83 |

* cited by examiner

*Primary Examiner* — Minnah Seoh
(74) *Attorney, Agent, or Firm* — Intrinsic Law Corp; Ibrahim M. Hallaj (57) ABSTRACT

A method and system for providing a form record and for processing the same. For example, a medical record form in a clinical or hospital environment is provided based on user input and is processed upon the user's filling in of the form. In some aspects, a user indicates by way of a user interface a type of patient complaint and selects a type of medical record form that is to be used in conjunction with examining the patient. The system guides the user and accepts the user's inputs and provides a suitable medical record form from a plurality of form types. The selected form is printed, and used by the medical staff in the examination of the patient. The filled form is then returned to a processing station for scanning, where information in the filled form may be extracted and where the filled form may be added to a patient medical record or archive, or shared with another person or organization.

9 Claims, 8 Drawing Sheets

SYSTEM AND METHOD FOR FORM RECORD PROCESSING

TECHNICAL FIELD

The present application relates to creating, providing and processing form records such as those relating to patient medical conditions, treatments, and patient medical files.

BACKGROUND

It is a long-understood principle of healthcare to create and keep up to date and accurate records relating to the intake and care of patients. Traditional systems rely on hand-written records kept by caregivers. For example, a hospital or clinic might have paper forms that were set up by an administrative intake staff member and which identify the name, age, and gender of the patient, and perhaps the symptoms and appearance of the patient. A physician would then use the form to write thereon further comments, diagnoses, and recommended actions according to the observations, testing, and conclusions of the physician. A file and its content would be created into which the form was placed. The file, archived by patient name or other identification number, would become a permanent patient record that could be referenced at a later date if the patient returned for other checks or treatments.

A paper copy of a patient medical record requires significant, and often expensive, space in which to store the file. It is difficult and expensive for a hospital that sees thousands of patients a year and which desires (or is required) to keep and archive the files to do so. File storage is therefore a logistical challenge and a real expense to all hospitals and clinical organizations. Also, increasing insurance and regulatory requirements require keeping the patient records for a long time, perhaps even after a patient is cured, transferred, or is even deceased. In addition, regulatory and governmental laws include requirements to protect patient privacy, and therefore the keeping of patient records is complicated by the need to keep the records safe and private, and the possibility of losing the same.

As to backing up the information in a traditional medical record, a photocopy of the physical patient file could be created from time to time (with the attendant effort and cost) for purposes of backing up the information. The original or backup copy may be stored off-site for safekeeping. Copies for insurance reimbursements, patient copies, or copies to be provided to another medical facility or care giver may also be reproduced, at a cost approximately linearly relating to the number of copies made. This copying and backup process is prone to the usual frailties of handling paper files and records, including the risks of loss of the original copies, the risks of misplacing documents in the wrong file, the risks of fire, flood, or theft, and so on. Also, the keeping and updating of paper patient records leads to losses when one or more sheets of paper in the file become transposed or left out of the file during handling. These losses are usually permanent, and the information lost as a result cannot be re-created reliably or with accuracy. Furthermore, even if the patient record could be re-created, the recreation would not carry the proper authenticity of an original.

Therefore, as in other fields of art, medical records have seen a trend towards digital record keeping (in electronic file formats) to replace the traditional paper file keeping. This is especially so in the field of medical records where the requirements for documentation and the physically disparate locations of the entities needing the files continues to grow. As an example, we briefly examine the record keeping operation of a hospital Emergency Department (ED).

Traditionally, the ED may include a medical record form dispensing station where paper copies of standardized intake and medical record templates (specialized blank forms) are stored and kept. This situation is fairly common in modern hospitals in the U.S. The blank forms are provided by vendors, with some vendors' products gaining wide acceptance so that practitioners may be accustomed to certain types of standard emergency medical records forms. Companies such as Patient Care Technology Systems, Emergisoft and T-Systems provide such templates and related supplies to U.S. hospitals for use in their EDs.

The traditional paper-based ED medical record station is usually set up with slots or shelves in a special cabinet or shelving unit, each slot containing one kind of ED medical record form that the ED staff knows how to use. When supplies of one form run low, a vendor or a staff member of the ED brings in new blank copies, or makes copies from a file that can be printed on a printer, or makes photocopies of an existing blank copy. However, invariably, the supplies of blank ED medical record forms do run out, usually at a time when the need is high and the staffing is low, and these paper forms tend to become disorganized, and can be placed into the wrong slot in their dispensing station, and so on.

The ED medical record forms are sometimes organized by malady, body organ, or area of the body, including spaces for selecting standard responses or conditions and spaces for making brief notes. A patient complaining of some condition in a body organ or area is interviewed by a physician who fills in various information into that ED medical record form. When the physician is done filling the form, the filled form is then processed by the hospital staff, and may be sent to a data processing center for copying or scanning into an electronic database.

As an example, a patient with abdominal pain is admitted to the ED. The physician or a staff member is alerted to the patient's complaint and takes a copy of the abdominal pain related ED medical record from the dispensing station. The form assists the practitioners in their examination and diagnosis of the patient, and organizes the information discovered in the patient examination. The ED medical record form becomes part of the patient's medical record or file.

Figure 1:
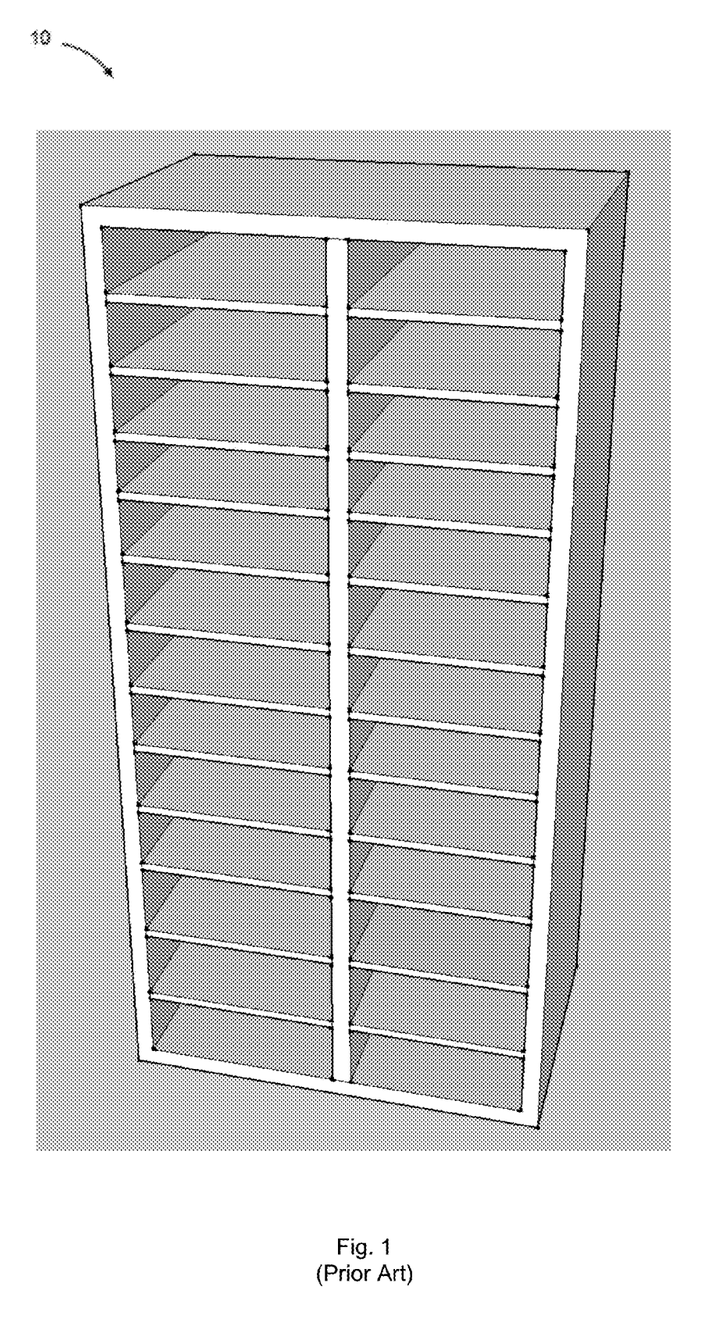
FIG. 1 illustrates a typical paper-based medical record form template dispensing station.

FIG. 1 illustrates a typical ED medical record form dispensing station at a well-run hospital. The station comprises a number of shelves that hold blank template forms as discussed above, each of which addresses a common or expected condition in incoming patients. It can be seen that the present paper-based forms can be an organizational challenge: to keep the forms in stock, to avoid transposition or accidental misplacement in the slots, and so on. Also, if the ED decides to add a new form or reorganize the placement of the forms, this requires re-building or re-organizing the shelving space to accommodate a new slot in the desired place, and then the staff need to be alerted to this change.

It has not been possible or practical so far to develop economical, reliable, effective electronic substitutes for certain types of medical records and files. Some attempts to digitize the intake and treatment records for hospital emergency rooms have been less than optimal. For example, in some cases, workers are required to carry about fragile and expensive equipment such as tablet computing devices onto which the intake and records are taken. This equipment is prone to failure, loss, breakage, and other hazards of portable electronic equipment in an emergency department (ED) environment. Also, if such equipment is compromised, it may allow unwanted access to or loss of sensitive patient and hospital data. Other examples require treating physicians to interview patients and then proceed to a location where a computer terminal is present. This can result in imperfect transfer and entry of information into a patient's records if the physician forgets an important detail during this transaction, or if the physician is distracted on the way to making the entry, which is a common occurrence in practical situations in busy EDs.

The present disclosure addresses this issue and provides a number of embodiments that are helpful in situations such as those described below and beyond.

SUMMARY

A method and system for generating, providing and processing form records (for example, medical record forms in a clinical or hospital environment) is provided. In some aspects, a user indicates by way of a user interface a type of patient complaint and selects a type of medical record form that is to be used in conjunction with examining the patient. The system guides the user and accepts the user's inputs and provides a suitable medical record form from a plurality of form types. The selected form is printed, and used by the medical staff in the examination of the patient. The filled form is then returned to a processing station for scanning, where information in the filled form may be extracted and where the filled form may be added to a patient medical record or archive, or shared with another person or organization.

Some embodiments are directed to a system for processing information, including a data storage apparatus for storing a plurality of pre-configured files representing a corresponding plurality of forms; a user interface apparatus adapted to receive inputs from a user of said system, including being adapted to receive an input to cause selection of a selected form from said plurality of forms, and adapted to provide an output to said user; a printing apparatus for providing a printed form by printing said selected form; a sensor apparatus for sensing markings made onto said printed form; and a adapted to process instructions for interpreting the sensed markings made onto said printed form.

Other embodiments are directed to a method for processing form documents, including providing a user with choices on a computerized user interface; receiving one or more inputs from said user through said computerized user interface responsive to said choices; processing said inputs to determine a selected form from a plurality of available forms; printing said selected form on a printing apparatus; receiving a marked-up copy of said form and processing markings on said marked-up form so as to derive information from said markings; and processing said information derived from said markings.

Yet other embodiments are directed to a method for generating a copy of a medical record form, including providing a computing apparatus designed and configured for placement within a medical facility; providing a touch-sensitive display apparatus with said computing apparatus that receives touch inputs from a user and provides visual output to said user; providing a user interface on said touch-sensitive display apparatus prompting said user to enter information relevant to a condition of a patient; accepting said input from said user including said information relevant to said condition of said patient; associating said condition of said patient with an electronic file corresponding to a medical record form associated with said condition; and printing a copy of said electronic file on a printing apparatus coupled to said computing apparatus.

BRIEF DESCRIPTION OF THE DRAWINGS

For a fuller understanding of the nature and advantages of the present concepts, reference is made to the following detailed description of preferred embodiments and in connection with the accompanying drawings, in which.

DETAILED DESCRIPTION

Figure 2:
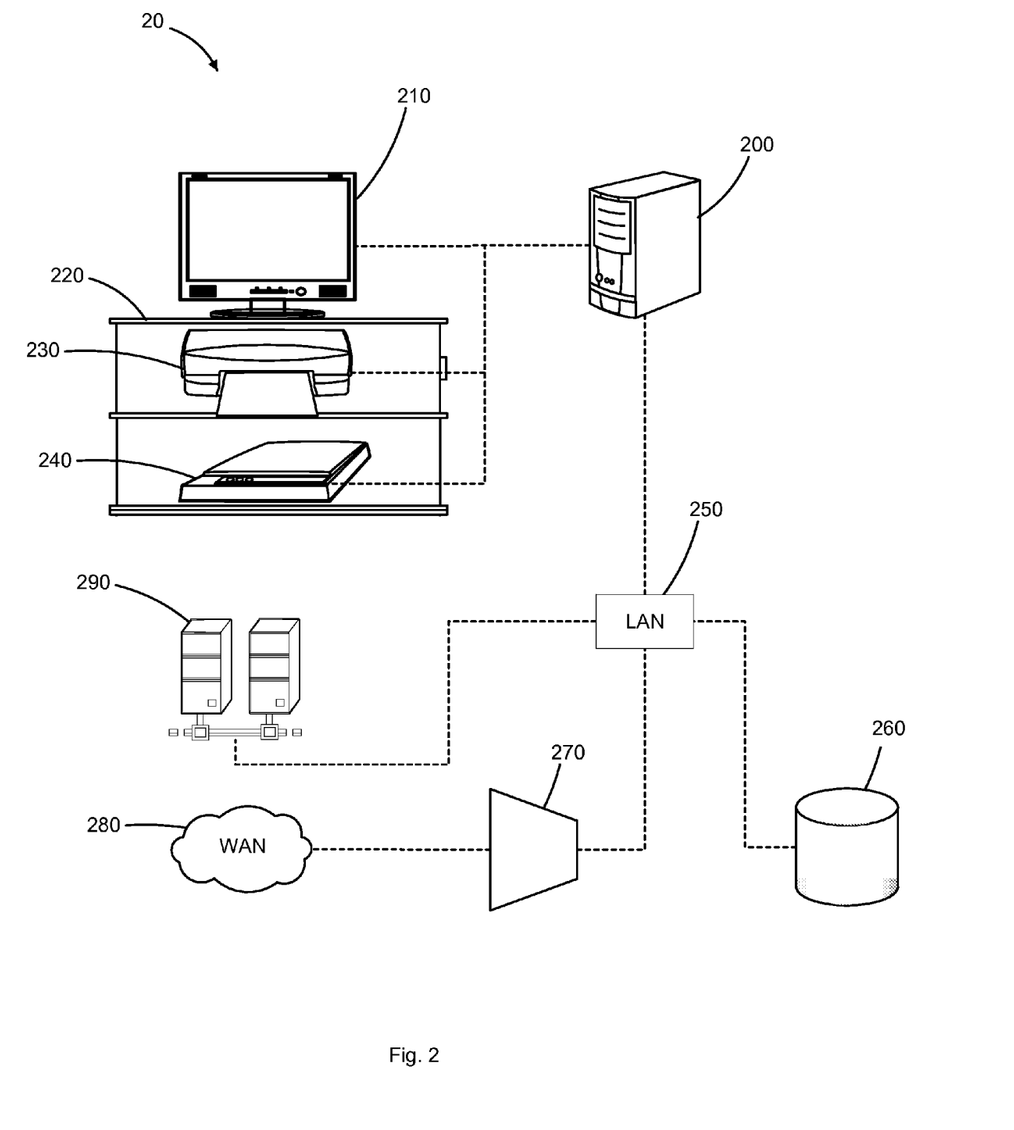
FIG. 2 illustrates a schematic architecture of some exemplary configuration of components of an electronic medical record processing system.

FIG. 2 illustrates an exemplary configuration of components of an electronic medical record processing system 20. The system includes a processing apparatus, computer, or workstation 200 that has an electronic processing circuit, memory, and other hardware adapted for processing data and executing instructions or software to support the operation of the system.

Computer 200 is coupled by way of one or more wireless or wired connections, indicated by dashed pathways, to other components of the medical records processing system. These include a viewable display apparatus 210, some input/output apparatus, which in the present example is at least partially co-located with display apparatus 210, for example, as in a touch-screen display that permits a user to enter and select information from the touch-screen display 210 using his or her finger or a suitable pen, stylus, or other device. The touch-screen display 210 shows the user a viewable user interface, and allows the user to interact with the system 20, as will be discussed below. In some embodiments, display 210 shows a plurality of selectable medical record options that substantially replace the plurality of paper-based shelves mentioned above.

A printer 230 is also coupled to computer 200 and is used for printing hard copies (paper copies) of forms and other things selected by the user using touch-screen display (or other input/output apparatus) 210. A scanner 240, which can be a flatbed scanner or another type of apparatus that takes a sheet with printed and written entries thereon and converts the image of the sheet to an electronic format, is also coupled to computer 200. As known to those skilled in the art, printer 230 and scanner 240 may also include their own processing units, communication units, input/output buttons, and other components.

For convenience, the touch-screen display 210, the printer 230, and the scanner 240 may be physically located near one another. For example, the display 240 may be at about user eye level, and the others may be located below the display in a secure storage unit 220. Though this arrangement is not required. In other embodiments, a support member supports the various components of system 20 that are most commonly needed by its users. As an example, the components of system 20 above may be integrated into a wall or wall-mounted using appropriate mechanical mounting parts so that they are conveniently located in the facility but yet not interfering with the movement of the facility staff. In some embodiments, the medical records station is provided as a kiosk, or as a dispensing unit. The kiosk or dispensing unit may be fixed in place, mounted to a wall, mounted on a support structure, or may be housed in a cabinet. In some embodiments, the cabinet housing the system or elements of the system may be mobile (e.g., on rolling wheels) so that it can be moved to a convenient location, or transported for repairs, and so on.

Computer 200 may be connected to other information machinery and network components using a communication module in computer 200 (e.g., a network interface card), which may be coupled to a local area network (LAN) 250, which is in turn coupled to other components and machinery and networks. In some embodiments, a database 260 is coupled to the LAN 250 and permits access to the database 260 by computer 200. Also, a firewall 270 may be connected between LAN 250 and an external wide area network (WAN) 280, securing the integrity of the data within the firewall 270. The WAN 280 may be used to send or receive information to or from outside data centers, medical facilities, agencies, vendors, government, educational, commercial, accounting, the Internet, or other hospital or institutional infrastructure. Other computer systems 290 may be connected to LAN 250 within the same organization or clinical facility as computer 200.

In all, system 20 allows for creating suitable medical record forms for use in a medical treatment environment such as an emergency department or other department in a hospital. The forms are selectable on touch-screen display 210 using a suitable interface as will be presented below. The forms are chosen by the staff member and printed on printer 230. Once filled out by the medical staff member, the filled forms are placed into scanner 240 for scanning into an electronic file format. The electronic file may include data suitable for optical character recognition (OCR), machine-readable formats, fill-in bubbles, answers selected by circling one or more available choices on a form, and other scannable or detectable markings on a machine-processed form, or bar code, so that the information from the filled medical record form can be searched or otherwise processed by information machinery, computers, database software, regulatory and accounting programs, and so on.

Figure 3:
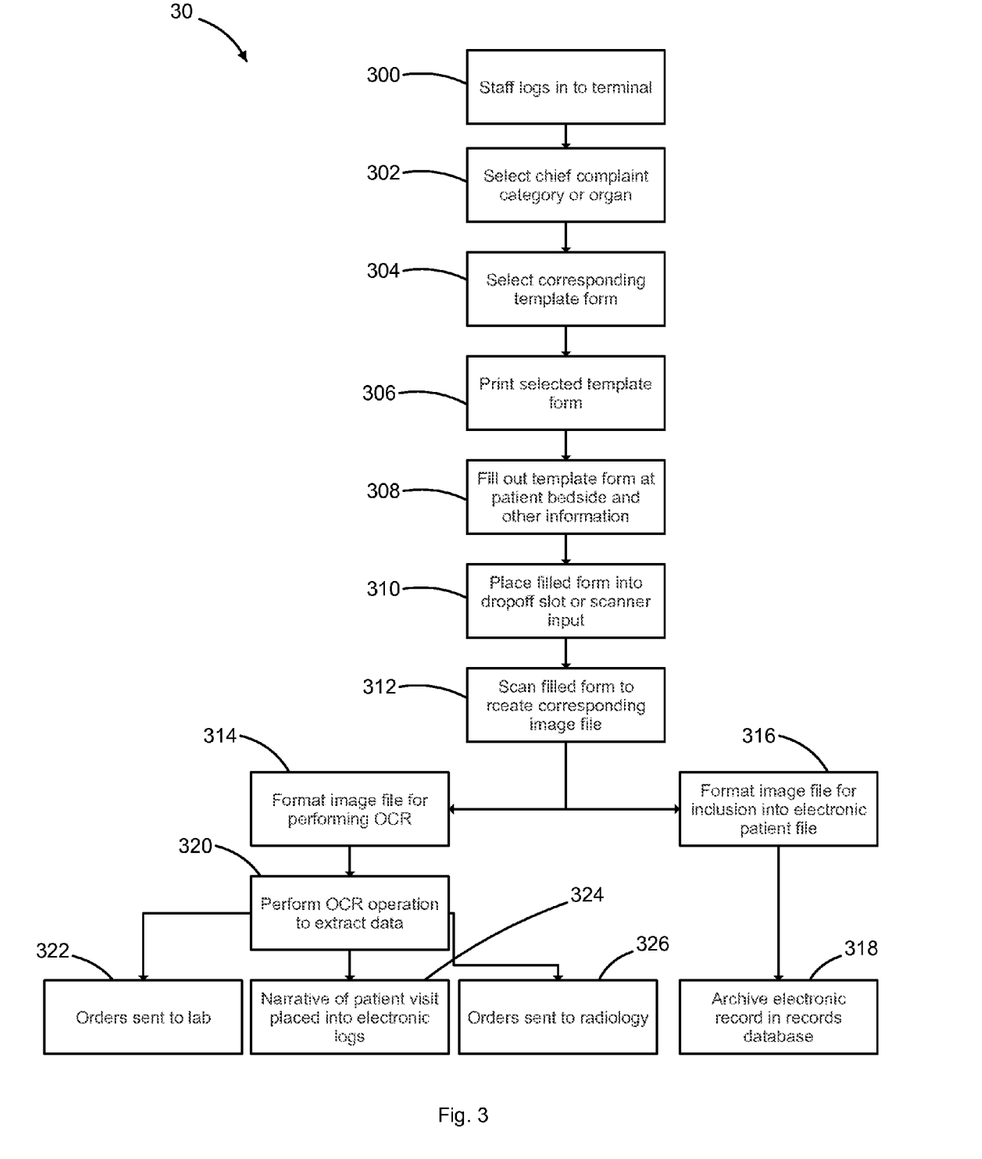
FIG. 3 illustrates an exemplary set of steps in providing and processing a medical record form.

FIG. 3 illustrates an exemplary set of steps carried out in a method 30 according to some embodiments of the present disclosure. A staff member, such as a physician at a hospital, logs in to the electronic medical records processing system at step 300. This may be done by using an approved user name and password, or by entering some personal or secret or unique code into an appropriate input field on the system's touch-screen display, etc. Other ways to authenticate the permission level and identity of a user are also possible, such as through a biometric scan (e.g., retina scan, face recognition, voice recognition, fingerprint pad). Other embodiments may provide a magnetic or electronic readable tag or ID card, a radio-frequency (RF) identification chip, keychain apparatus, or other sensor-based identifiers. It is not necessary in all embodiments that the medical records station require a log-in step. In some instances, the nature or location of the station may be secure enough to remain unlocked.

Once the staff member or physician has access to the controls of the electronic medical records processing system, e.g., once logged into the system, the display presents a screen of information to the user. For example, the screen presents options for various medical record template forms that the user may need. Also, the screen may display navigation or status information relating to the user using the system. The elements of the system may present the user with options for navigation so that the user can select a chief complaint category or organ type at step 302.

At step 304, the user may select a template form corresponding to a complaint or to an organ, region of the body, or other indicator. The selected template form may be shown on the display screen so that the user can confirm his or her selection, and is then printed at step 306 using a printer connected to the processing station and/or the computer controlling the medical records station. The printed form may have elements pre-filled in by the computer software such as the provider's name, the date and time, etc. In addition, the form may be pre-filled with data particular to the patient if they have been identified by scanned sticker, patient name selected on-screen or another method when the form is chosen. In this case, the printed form may also then contain information such as patient name, date of birth, and vital signs, allergies, past medical history, arrival time, etc., which may be imported from other networked software that is already in use in the ED.

The physician responsible for seeing the patient takes the printed template form and conducts his or her business at the patient's bedside as normal. The physician fills in certain information about the patient generally, and also fills in information following examination of the patient and following a conversation with the patient about his or her condition at step 308. Recommendations and observations are recorded in appropriate places on the medical record template form. The physician may also place a signature or a seal on the form.

When the physician is finished using the form and the form is filled out, the form is returned to a collection location. At step 310, the filled form is dropped off at the electronic medical records processing station, which may be the same or different from the station where the form was selected and printed. The form may be placed into an "in-box" type container for processing later in some embodiments. However, in other embodiments, the filled form is processed substantially at the time it is dropped off at the processing station. Here, the form is placed into or onto a scanner at step 312, which scans the visible content of the form into an electronic file of a given type.

The electronic file obtained by scanning the filled form is formatted at step 314 for optical character recognition (OCR), or prepared in another way for machine processing, such as making optically scannable markings, circling of choices, underlining choices, crossing out non-selected options, filling or checking a check-box, etc. In some embodiments, an original (prior to filling in by the physician) image or representation of the form is electronically subtracted from an image or representation obtained after being filled in, and the result of the subtraction or cancellation is used to determine the markings and choices indicated by the physician on the form. An OCR step is performed on the formatted electronic file at step 320. Many useful operations can be carried out on the results of the OCR of the form. These include sending corresponding information to a lab ordering system at step 322, or creating a text-based narrative for entry into a log at step 324, or sending out orders to a radiology ordering system at step 326.

Alternatively, or in addition, the results of scanning the filled out file may be converted into a standardized image format (e.g., JPEG, TIFF, PICT, BMP, or PDF). Also, the file may be formatted for inclusion into an electronic patient file at step 316. The electronic patient record may be processed for storage on-site or off-site, including by archiving the file in a records database at step 318. It will be appreciated that filtering, compressing, and encrypting the file or its contents are possible in order to reduce the storage requirement for the electronic information or to better secure its confidentiality.

As discussed earlier, the electronic medical record processing system may further transmit some or all of the information from the filled form to another computer, another lab, another physician, an accountant, a medical records processing office, or a radiology or lab testing facility. This may be done substantially at the time that the examination of the patient is completed and when the filled form is deposited back into the system for processing. In this way the rest of the hospital staff, e.g. in a recovery ward, and others may use and see the results of the examination conducted by the physician who performed the patient intake or examination (e.g., in the ED of the hospital).

By way of example, and as an illustrative aid to understanding the present concepts, we move to what exemplary embodiments of the present system might appear as in use. These methods comprise steps that may be enabled by or performed using hardware executing software programs provided in the form of machine-readable instructions. The software code or programs running on the present systems may be embodied in computer source code or object code or executable instructions or logic that can be stored on or in a computer-readable medium such as an optical or magnetic medium. The system may comprise a processor or processing system that can receive the executable instructions or code to cause a transformation to an input/output apparatus coupled thereto (e.g., a display panel or data residing in a data storage medium).

Figure 4:
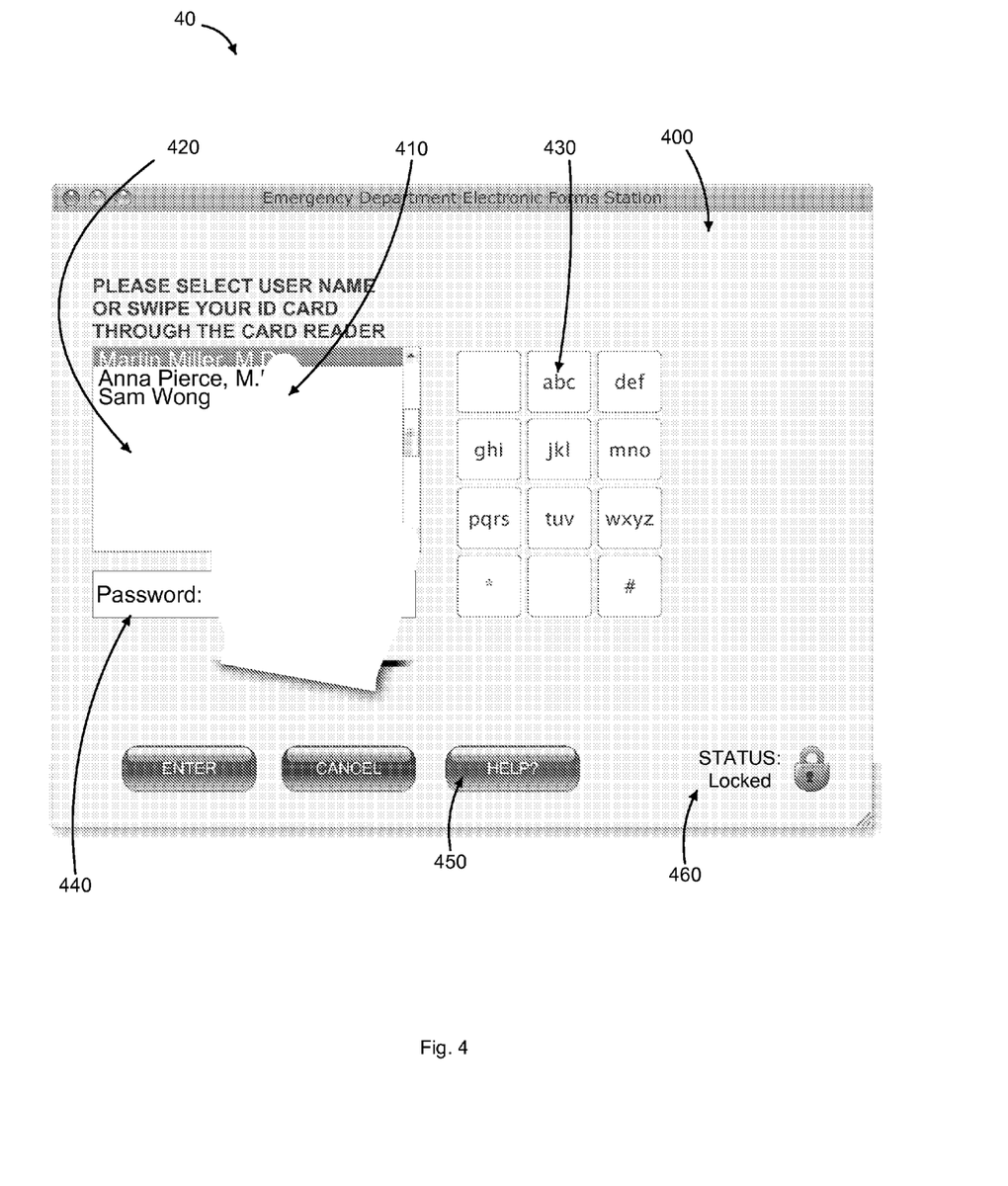
FIG. 4 illustrates an exemplary user interface for identifying a user of the medical records dispensing station.

FIG. 4 illustrates an exemplary login screen 40. The login screen is presented so that a user can be authenticated for access to certain information and functions of the system. A window-based interface 400 may be used to interact with the user of the system. The user uses his or her hand or fingers 410 to cause action and make selections on the input/output device of the system, for example, on a touch-screen interface.

The user selects his or her name from a User Name listing 420 of known users that may log into the system. There are a number of ways to do this, including by allowing the user to type in their user name into a keypad, or by choosing from a plurality of users in a user interface module such as 420, which may employ text entry elements, pull-down menus, scrolling selection modes, etc. Again, a user may automatically be logged in or identified by the system by way of an electronic, optical, or magnetic apparatus such as a card, key, bar code, biometric input, or other means that allows the system to determine the identity of the user. In some embodiments, soft keys (or hard keys on a keyboard) 430 may be presented to the user with alphanumeric associated values so that the user can type in his or her name or can drive the selection of the user's name from a pre-existing list 420. Once the user has finished using the alphanumeric keys 430, these may be replaced on screen 400 with another set of keys, as will be described below by way of illustration.

Once the user 410 has indicated his or her name in user interface module 420, he or she proceeds to entering a password into a password entry user interface module 440 to complete the authentication process. A status message 460 may be indicated on the display, e.g., indicating that the system is locked prior to completion of the login process. Those skilled in the art would appreciate the myriad user interface modifications, extras, and appearance and feature sets that are possible to modify or augment or enhance the simple example provided herein. For instance, a user interface widget such as a Help button 450 may be provided to seek instructions to assist the user in using the system. A Cancel button may be provided to go back one or more levels in the use of the system or in case the user entered an incorrect piece of information into the system.

Figure 5:
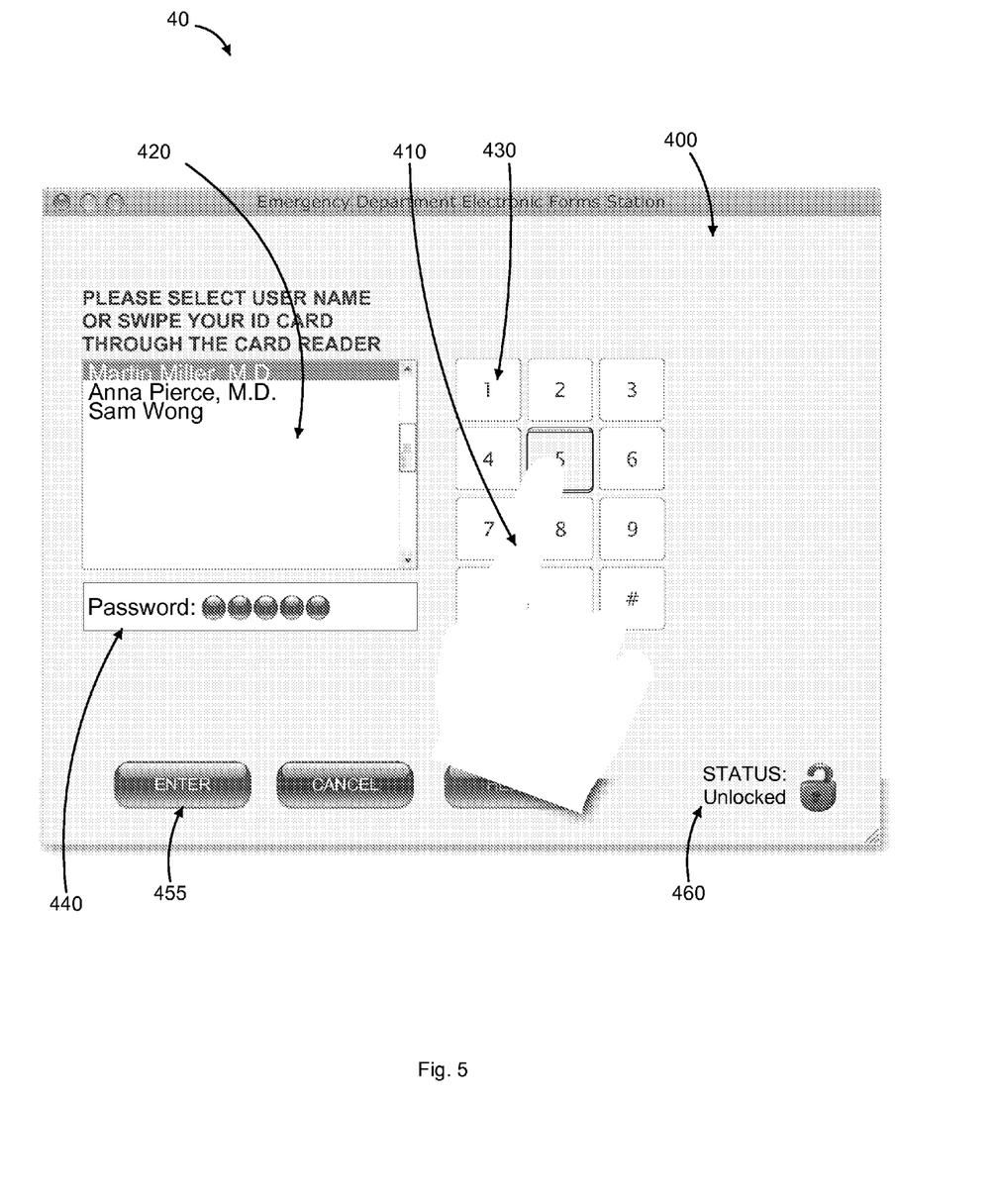
FIG. 5 illustrates an exemplary user interface for authenticating the user of the medical records dispensing station.

FIG. 5 illustrates a user 410 entering his or her password or unique log-in code into the system's user interface 400 to complete the authentication of the user. A number pad may be provided with a plurality of numerical (or any other, e.g., alphanumeric or combination) values associated with buttons or keys 430 the number pad. The user uses his or her finger 410 to type in and select his or her password, which may appear in data box 440, or may appear in an obscured form to prevent unwanted observation of the password by others. Visual and/or audible feedback (e.g., changing the appearance of a button or playing a brief sound when a button is touched) may be used to assist the user in using and appreciating his or her actions on the user interface 400.

If the user enters incorrect information to log into the system, an error message of some type may be provided, a visual and audible signal may be generated, and even, a log entry may be made indicating the attempt. If the user is successful in logging in (enters an appropriate user name and password) the system may automatically unlock itself, and the status indicator 460 may reflect this condition. The user may also press an "Enter" button 455 when ready, or indicate that the logging in process is complete by some other method as deemed suitable by those implementing the system.

In some embodiments, the user is provided by the hospital with a digital key card, RFID encoder, key, or other magnetic or biometric device for authenticating the user. For example, the hospital may issue ID cards to its staff, the ID cards including a magnetic "swipe" card feature so that the staff may merely run their ID cards through a compatible reader slot that reads the staff's user name and other authenticating information. To avoid the risk of use by unauthorized users if ID cards are stolen or lost, the system may accept the swipe card as an identifying input, but still require a personal code to be manually entered into the user interface screen to complete the process. Additionally, other biometric identifying methods, such as scanning a user's face, eyes, or fingerprints can be used for authentication.

Figure 6:
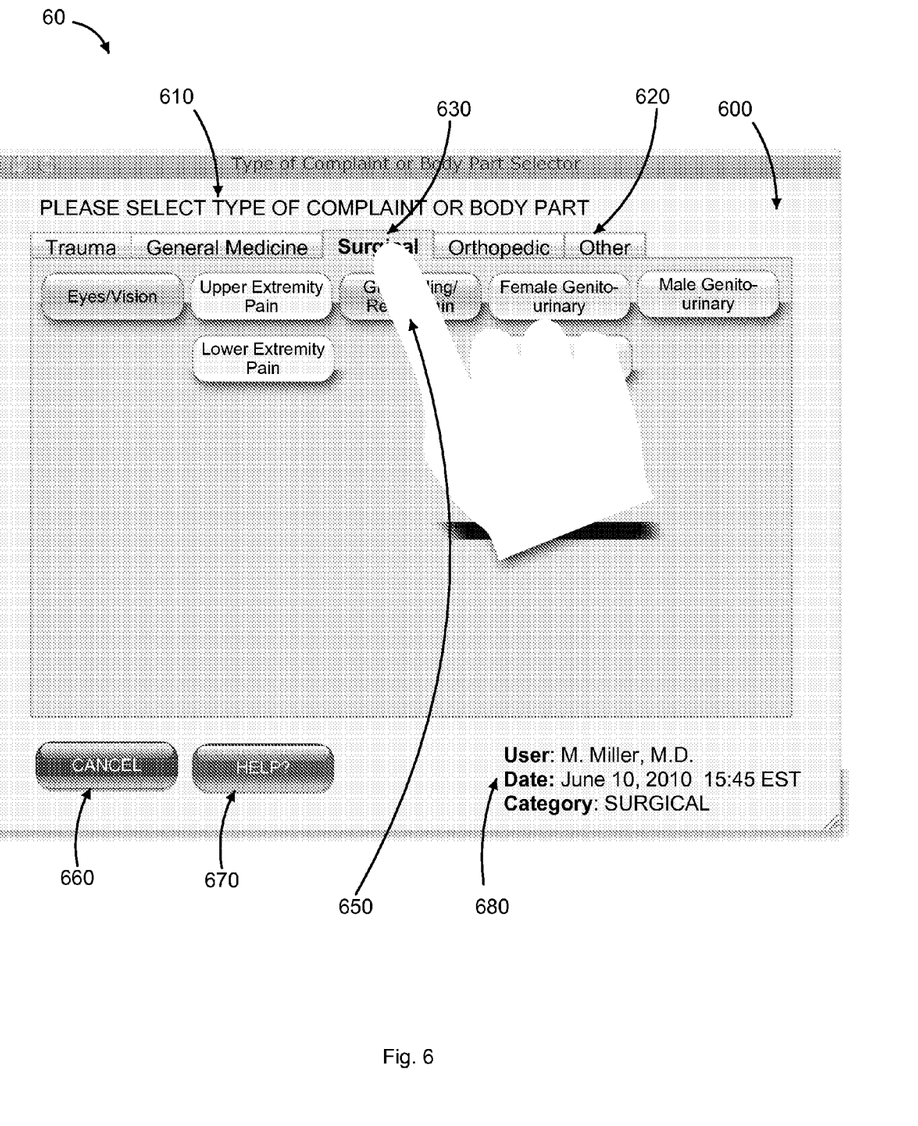
FIG. 6 illustrates the selection of a type of patient complaint or afflicted body part from a group of such types.

FIG. 6 illustrates an exemplary mode of the system 60 in which the user selects a primary complaint or body part of the patient. User interface 600 presents a user with visual elements indicative of various types of patient complaints and body parts that may be injured or diseased. The presentation may be organized in a number of ways, but is preferably shown to the user in a clear way that simplifies the selection process and is usable under daily clinical conditions.

In one embodiment, a group of tabs 620 (e.g., Trauma, General Medicine, Surgical, Orthopedic, Other) labeled with their main complaint and body part types are presented. By indicating, clicking, pressing, touching on, pointing to, or otherwise actuating a desired selectable one of said tabs, a user 650 chooses the type of complaint or body part most relevant to the patient's visit. A message area 610 may help the user by instructing the user as to what action is expected from him or her. Here the user is instructed to select a type of complaint or body part from those available in tabs 620. A Status area 680 may indicate any of numerous states of the system or other helpful information. Cancel button or widget 660 allows the user to cancel an operation or exit to a previous screen. Help button 670 provides context-sensitive instructions and help to the user.

In the illustration, the Surgical tab 630 is chosen. A helpful sound (e.g., a click) may be generated by an audio component of the system, or a voice synthesis module may play a sound or a voice indicative of what action has been taken as an aid to the user. Once selected, the tab 630 may take on a different (highlighted) appearance, for example by accentuating the tab's color or text font. Also, once selected, the display of the system shows one or more selectable sub-categories of complaints or body parts as will be described next. Note that these interfaces may take on one of numerous forms, and are not limited to the tabbed format, but may alternatively be presented as text dialogues, drop-down menu options, pop-up features, or other context-dependent audio or visual widgets, as desired.

Figure 7:
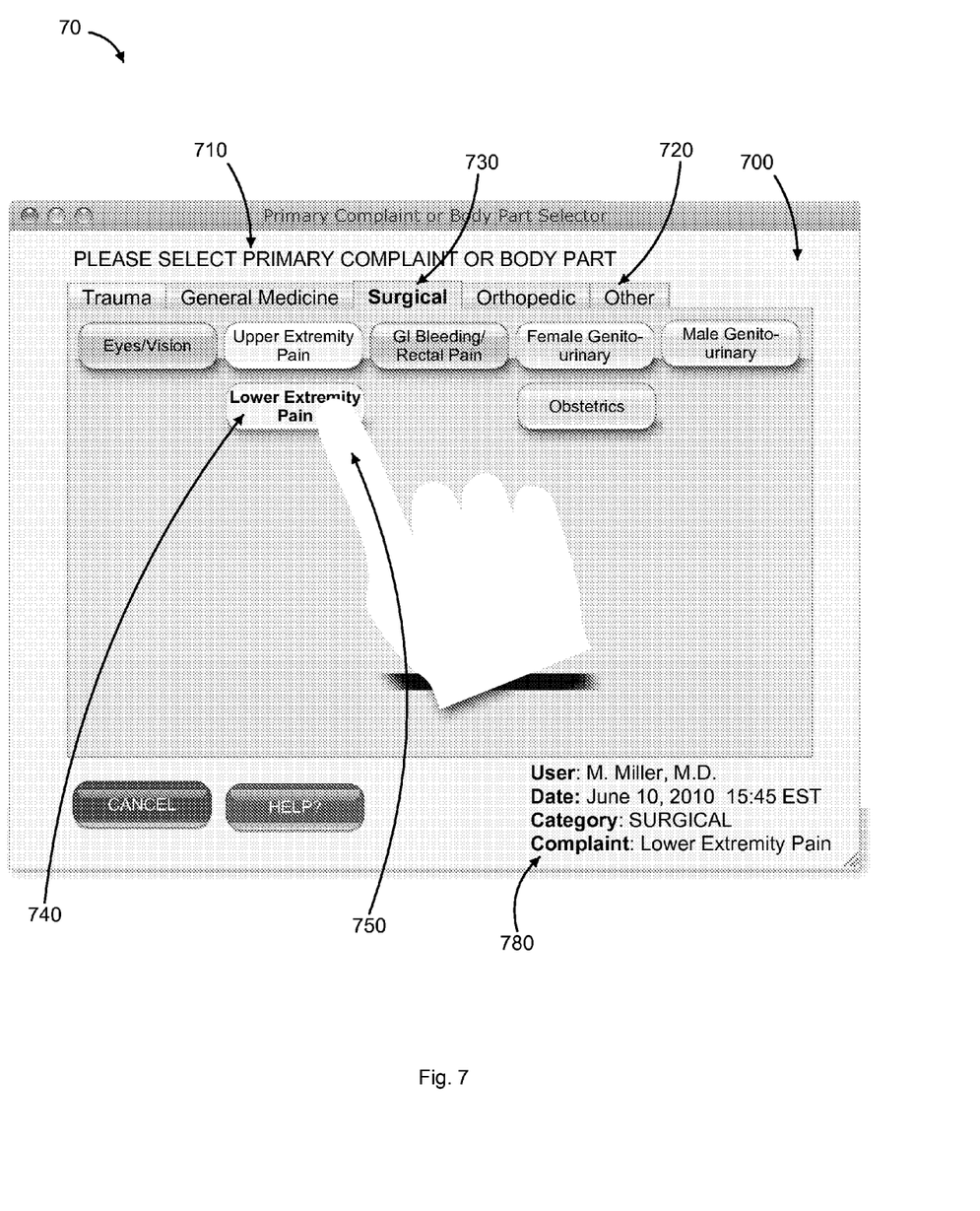
FIG. 7 illustrates the selection of a primary complaint or afflicted body part, which is used to generate a medical record form for use in examining or diagnosing the patient.

FIG. 7 illustrates a mode of the system 70 used to choose the primary complaint or body part from which the patient is suffering, and which fall under the category or type of complaint that the physician had chosen from tabs 720. Now that the physician (user) has selected the type of complaint (e.g., Surgical) as described above, the user can choose from a plurality of primary conditions within the indicated type of complaint or body part. As an example, the Surgical tab 730 lists "Eyes/Vision," "Upper Extremity Pain," "Lower Extremity Pain," "GI Bleeding/Rectal Pain," "Female Genito-urinary," "Obstetrics," and "Male Genito-urinary" primary complaints and body parts. The user presses with his or her finger 750 in the example of a touch screen interface to select one of the available options. For example, the user selects "Lower Extremity Pain" 740. The selected option can be chosen by pressing a button, drop-down list, pull down menu, or other user interface feature. Again, once selected, the user's selection 740 may be highlighted visually or audibly to confirm its selection. For clarity, the various tabs and selection buttons may be color-coded or shaped or sized or located with respect to one another on the user interface so as to prioritize them or indicate some other special or common feature thereof. For example, all female maladies may be coded and displayed as pink, and all male-specific conditions may be displayed as blue, and so on. As before, Cancel, Help, Status, and other informational and user interface features may assist the user.

Note that with each successive level or screen of the user interface, the Status message area 780 may be updated to reflect the present condition of the system. This information may be printed onto the printable electronic medical record forms that come out of the printing station to be taken to the patient area during the examination of the patient. This can save time and improve accuracy in the filling of the forms, as the physician's name, the date and time, and other useful information can be filled into fillable spaces on the template forms by the system prior to printing the forms.

In some embodiments, once the user selects the primary complaint or body part as in FIG. 7, a corresponding paper form is printed out by the printing apparatus. The printed form may include as much information (pre-filled) as possible by virtue of the physician having already identified themselves, the time of day, the identity of the patient if already entered into the system, and so on. If no specific information has been entered, then a fillable generic form is printed and the physician or staff member would fill in all applicable information by hand at the patient's bedside or elsewhere before returning the form for scanning and processing. Note that a number of types of entry may be provided on the form, such as bubble fill, check boxes, circling of one or more choices, crossing out one or more undesired options, underlining, and so on. As stated before, these entries may be detected by a suitable apparatus, e.g., an optical or magnetic sensor, and can determine the markings and entries made. In some embodiments, the original form's image or representation may be subtracted from the marked up (filled out) form's image or a representation thereof to obtain the markings and selections made to the form.

Moreover, it is not required in some embodiments for the hospital staff or physician to log in to the system or authenticate themselves or even identify themselves. For example, if there are visiting staff that don't have ID numbers or cards, or that are not known to the system, it is possible to just select a "VISITOR" or "Non-Staff" button on the system's home screen, which will still allow the selection of and printing of blank fillable medical record template forms, albeit without any special information pre-filled.

Figure 8:
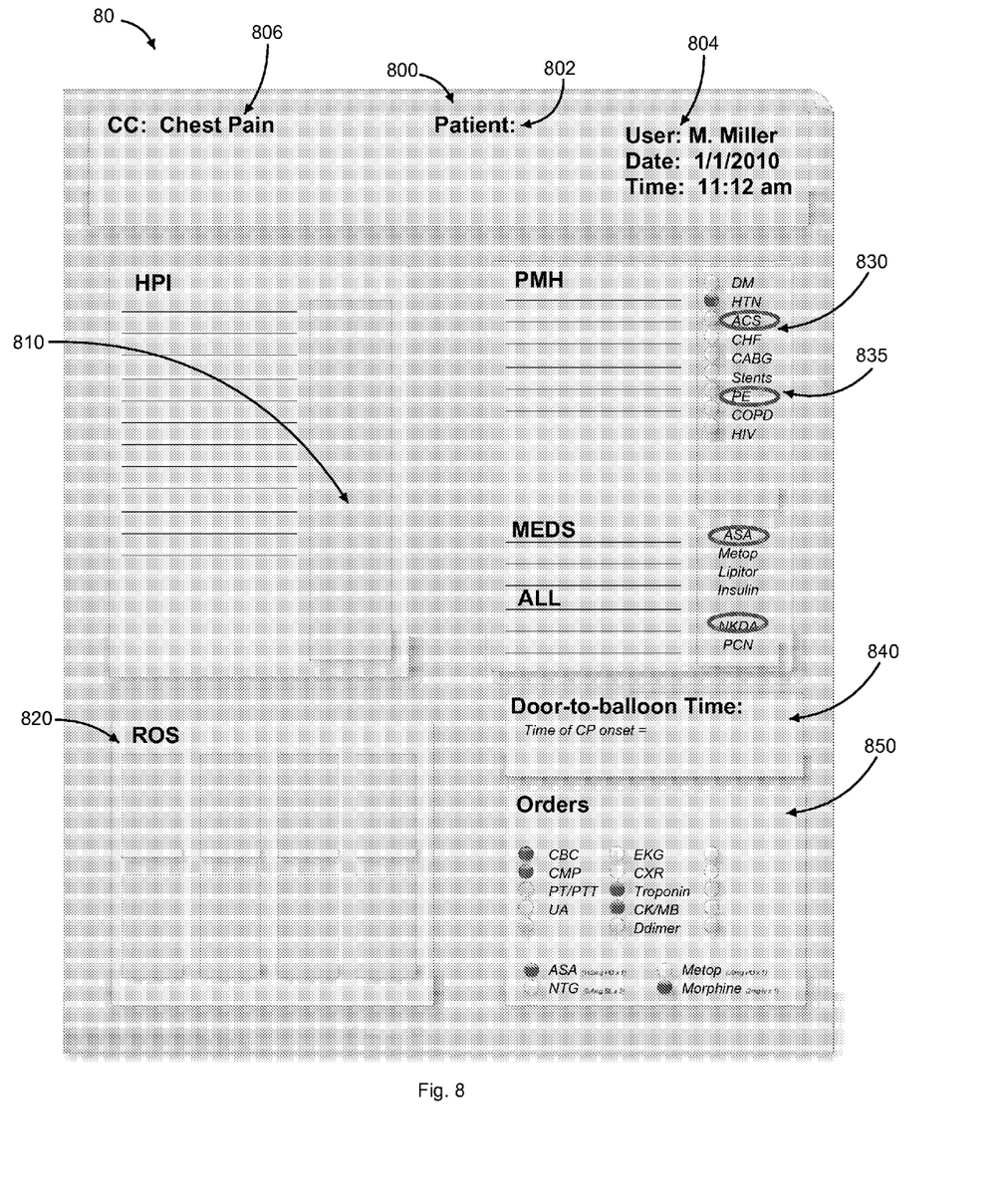
FIG. 8 illustrates an exemplary medical record form printed by a printing apparatus of the present system.

FIG. 8 illustrates an exemplary medical record form 80 as may be printed out on a printing apparatus of the above system. One or more sheets of paper 800 are provided, which may be printable on one or both sides thereof, depending on the amount of information relevant to the specified malady. The following example is of course not by way of limitation, and the formatting, appearance, specific details, and other aspects of the forms 80 are configurable as needed.

An identification section containing a patient identification number or name 802 is included in form 80. Also, the identity of the treating physician, date, time, and other information may be printed or written into the form at 804. As mentioned earlier, if some or all of the above information is available to the system, e.g. by virtue of the physician log-in, this information could be pre-printed into the associated spaces in form 80. Also, some of the above information may be typed, entered, or written in at the time of admitting the patient by a staff member.

Various blocks of information, as appropriate for the primary complaint or body organ, are included in the form 80. For example, a section 810 (HPI) may include space for writing details of various kinds and physician observations, notes, or recommendations. A second area 820 of the form 80 may be color-coded or shaded to distinguish elements thereof as relating to order entry, legal, billing, insurance, or other decision making elements or formalities. Yet another portion 830 of form 80 may include options that are to be selected, checked off, or darkened in (e.g., bubble form sections) so they can be scanned by an automated machine to read the entries therein. The physician may also use a pen or pencil to circle one or more items from a list of options or selections in portion 835 of form 80.

Form 80 may also include a portion for entry of "Door-to-Balloon Time" (indicative of the efficiency of the hospital ED and its response time to certain cases) or time of chest pain onset (indicative of the effectiveness and speed of responding to a myocardial infarction case). Another section 850 of form 80 may include selection options that the hospital staff and physicians can use to order common lab, radiology, pharmacy, or other orders with by circling or indicating the associated bubbles.

In some embodiments, one or more machine-readable calibration marks may be included in the printed medical record forms. For example, one or more markings can be printed at or near a margin or corner of the forms so that proper positioning of the forms can be accomplished during scanning or reading of the forms. In certain cases, alignment, re-sizing, rotation, stretching, or other image processing operations may be performed on the processed forms using the calibration markings, for example using image processing or matrix operations.

One-dimensional or two-dimensional bar coding may be employed in printing the medical record forms. This technique may enable identification of a patient or other information about the patient. The bar codes and machine-readable calibration marks above may be printed on a front face or on a back face of the forms, as appropriate. Other information may be encoded in the markings and bar codes or machine-readable marks on the forms. This information may in some cases improve the effectiveness of the medical record processing. In some examples, using a bar code or machine-readable marking can improve privacy or security of the information, as the machine-readable codes would be less detectable or readable by unauthorized human beings if the filled forms are misplaced, lost, stolen, or come into the wrong hands.

Various methods for efficient and effective and reliable machine processing of the forms may be employed. As discussed above, calibration and image subtraction may be used. In addition, noise reduction and machine intelligence algorithms can be employed to determine the best or correct intention of the person making marks onto a medical record form. For example, if a check box or fillable bubble entry is imperfectly marked by a person, the system can use such techniques for correcting the imperfection and determining the proper intended mark thereon. One such technique includes using a weighting algorithm to determine the proper pixels in an image belonging to a human-made mark or character. Thresholding and averaging and interpolating operations are also potentially useful for some embodiments to process and identify marks made on the forms. These and other methods may be employed to determine the intended underlining, crossing out, circling, and checking of choices available on pre-configured forms.

On forms that are designed to accept hand-written entries by a treating medical staff or physician, the forms may be scanned and a block image of the write-in area preserved as an image portion. Hand-made drawings or diagrams or other markings can be processed as images and stored in data storage apparatus connected with the system. Alternatively, the markings in the write-in area may be processed using optical character recognition (OCR) and other techniques mentioned above to determine the content thereof.

The forms may be processed by the sensors that scan or read the forms in discrete ways according to some embodiments. That is, one region or area of the forms may be processed in a first way (e.g., as an image), while a second area or region of the form is processed in a second way (e.g., as a fill-in or fillable bubble option, i.e., an icon or character such as a circle, oval or square that can be colored in by a user to fill in his or her choice), and a third region or area of the form is processed in a third way (e.g., by OCR operation on written text), and so on.

In some embodiments, the placement of information on a medical records form may provide a basis or an input for delivery of information derived from the form to a particular destination. For example, if a region or area on a form is designated as or identified to be for lab testing, then the information gleaned by the system from that region or area of the form may be routed to a lab ordering part of the system or to a communication apparatus or facility or branch of the hospital associated with lab orders. In another example, a portion of the form has entries related to pharmacy medication orders, and information obtained from this portion of the form is sent to a system or place that processes pharmacy orders. Other information may be flagged by its location on a medical records form and sent to a corresponding person, department, system, or agency for processing and/or storage such as radiology orders, consultation requests, which may automatically deliver a page to an on-call physician indicating the patient and his or her primary complaint or condition, including optionally a call-back number.

The present system and method is well-suited for a variety of applications. In several examples, the Emergency Department (ED) of a hospital may use the present concepts to improve the processing of medical record forms. It should be appreciated that other hospital and clinical departments and wards can benefit from the same or similar systems and methods. For example, in the use and processing of patient consent forms, insurance forms, patient intake and information sheets, procedure notes, consultation notes, progress notes, which can all benefit from the instant generation, distribution, processing and management of the associated paperwork. Additionally, the present concepts are also well-suited for other applications within and outside the medical records processing field.

Many benefits will become apparent to those skilled in the art upon consideration of the present disclosure. Savings in time, error reduction, improvements in security of patient information, storage and record keeping efficiencies, and other benefits are possible using various aspects hereof. In particular situations, a substantial improvement in processing and filing of form-based medical records becomes possible using the present concepts, wherein the present systems and methods facilitate generation of the appropriate health record form or chart, preparation of the same for a given use, and processing the same once it has been used for automatic or semi-automated inclusion into a patient's medical record. Still other applications hereof may include those for doctors' office papers, chart management, patient handouts and informational brochures, medication use instructions, multi-lingual medical forms and informational material, dental offices, psychiatric wards and practices, legal and banking records (e.g., mortgage forms, loan applications, bankruptcy, divorce, real estate, tax, and myriad others) may be generated and processed in a similar way. Even commercial estimates, drive-through services, car rentals, travel ticketing and reservations, recreational, educational, testing, and other such fields of use may benefit from some or all of the above improvements and innovations.

Furthermore, since the paperwork, forms, and records of interest are generated by a computer printing system in some examples, these may be modified by a person or automatically by a machine (computer) for a specific application prior to printing of the same. So for example, the present system and method permits the modification of the forms if needed so that new forms are printed in the modified new version, whereas existing paper-based form dispensing stations and systems must exhaust or discard the available stock prior to putting new forms into circulation. This is wasteful, and may lead to errors or inconsistencies if various forms stations and facilities are not using a same version of a given form at a given time.

Still further, the present system and method permits the updating of forms as needed from a remote or central facility. That is, when a correction or change is made to a form, the latest version of the form can be electronically delivered to each form dispensing and processing station, where the latest version of the form is immediately available for use and can replace the previous versions of the form without user intervention. This is useful if mistakes are discovered that require correction, or if a law or policy is updated requiring changes to a form, or if a pricing scheme printed on the form is updated, or if the availability or description of goods or services is changed, and so on. These updated or new forms can be included in the set of forms available to users of the station, and may be delivered to the station by way of a wired or wireless network, portable storage device, or another means of delivery of an electronic record or file to the station.

New or updated forms are not necessarily delivered to the stations by electronic means from remote locations. But in addition, in some embodiments, a "lead" or "super" user of the system may scan or feed in a hard copy (e.g., paper) of a new or updated or revised form, which can then be available to other users and appear as an option to the users of the system. The new form may be made to replace an existing option in the system, or it may be made available in addition to the previously available set of forms. A corresponding new icon or form name can be set by the lead or super user, and the new form thus provided can be stored into a storage device electronically following scanning of the same, and may then occupy the same or similar storage space in the system's memory device as the other system forms.

As discussed above, The present invention should not be considered limited to the particular embodiments described above, but rather should be understood to cover all aspects of the invention as fairly set out in the attached claims. Various modifications, equivalent processes, as well as numerous structures to which the present invention may be applicable, will be readily apparent to those skilled in the art to which the present invention is directed upon review of the present disclosure. The claims are intended to cover such modifications and equivalents.

What is claimed is:

1. A computer-implemented method for generating medical forms for the intake and care of patients as well as for processing of selected medical form documents upon their return to said processing station, comprising:

providing a log-in screen interface to a medical practitioner for secure logging-in to a medical forms processing station and authenticating log-in credentials from an authorized medical practitioner in a kiosk containing said medical forms processing station;

accessing a plurality of medical forms stored in said processing station in said kiosk and providing a medical practitioner with choices of medical forms representing patient conditions on a computerized user interface including a display screen in said processing station in said kiosk for dispensing and subsequent processing of said medical forms;

receiving one or more inputs from said medical practitioner through said computerized user interface in said kiosk indicative of a choice by said medical practitioner from among said provided choices;

processing said inputs in a processor apparatus in said kiosk to determine a selected medical form from a plurality of available medical forms representing a corresponding plurality of medical conditions;

printing said selected medical form on a printing apparatus in said kiosk, substantially at a time of selection of said selected form by said medical practitioner, including printing pre-determined markings relating to said selected medical form and printing spaces into which said medical practitioner can enter his or her markings relating to said patient;

receiving in said kiosk a marked-up copy of said printed selected medical form containing the medical practitioner markings and processing said medical practitioner markings on said marked-up form so as to derive information from said markings relating to a medical condition of said patient; and processing said information derived from said markings in a medical records processing system.

2. The method of claim 1, further comprising optically recognizing some or all of said markings to derive character-based information from said markings.

3. The method of claim 1, further comprising deriving graphical information from said markings.

4. The method of claim 1, further comprising routing information derived from processing said information to a destination based upon content of said information.

5. The method of claim 1, further comprising storing a representation of said marked-up form in an electronic records storage location.

6. The method of claim 1, further comprising receiving from and providing to a medical practitioner choices to select a medical record form from a plurality of medical record forms.

7. The method of claim 1, further comprising pre-populating said form with at least some information specifically relevant to an instance of use of said form prior to printing said form.

8. The method of claim 1, further comprising calibrating a scanned image of said form prior to processing the markings thereon so as to enhance said processing.

9. The method of claim 1, further comprising generating a text-based narrative description of a patient's condition for inclusion in said patient's medical record, said narrative derived from information entered by a medical staff member onto said form.

* * * * *